(12) United States Patent
Gentz

(10) Patent No.: US 6,860,611 B2
(45) Date of Patent: Mar. 1, 2005

(54) CAMERA AND LIGHT APPARATUS

(75) Inventor: Robert E. Gentz, Wheatfield, IN (US)

(73) Assignee: Robert Gentz, Wheatfield, IN (US)

( * ) Notice: Subject to any disclaimer, the term of this patent is extended or adjusted under 35 U.S.C. 154(b) by 0 days.

(21) Appl. No.: 10/186,452

(22) Filed: Jul. 1, 2002

(65) Prior Publication Data

US 2004/0001333 A1 Jan. 1, 2004

(51) Int. Cl.$^7$ .............................................. G03B 15/02
(52) U.S. Cl. ................................ 362/3; 362/8; 362/11; 362/18
(58) Field of Search ............................ 362/3, 8, 11, 18, 362/103, 109, 208; 396/28, 17, 199, 429, 431; 600/101

(56) References Cited

U.S. PATENT DOCUMENTS

| | | | | |
|---|---|---|---|---|
| 5,879,289 A | * | 3/1999 | Yarush et al. ................ 600/179 |
| 6,406,293 B1 | * | 6/2002 | Burnstein ..................... 433/29 |
| 6,432,046 B1 | * | 8/2002 | Yarush et al. ............... 600/179 |
| 6,554,765 B1 | * | 4/2003 | Yarush et al. ............... 600/132 |
| 2002/0044435 A1 | * | 4/2002 | Pohlert et al. ................ 362/13 |

* cited by examiner

Primary Examiner—Stephen Husar
Assistant Examiner—Anabel Ton
(74) Attorney, Agent, or Firm—Doreen J. Gridley; Alexander Forman; Ice Miller

(57) ABSTRACT

The present invention comprises a lamp assembly with an integral circuit to provide electrical connectivity to the lamp and methods of making the lamp assembly. The integral circuit in one embodiment is constructed from a conductive polymer. The polymer may be injection molded, and the lamp assembly housing and integral circuit may be manufactured using a two-shot injection molding process. The present invention may be used in the production of a wide range of lamp assemblies, including vehicle headlamp assemblies.

11 Claims, 7 Drawing Sheets

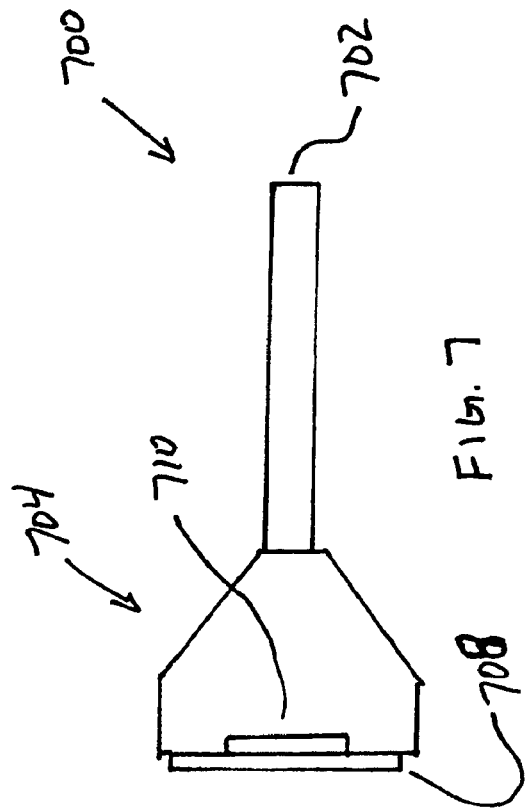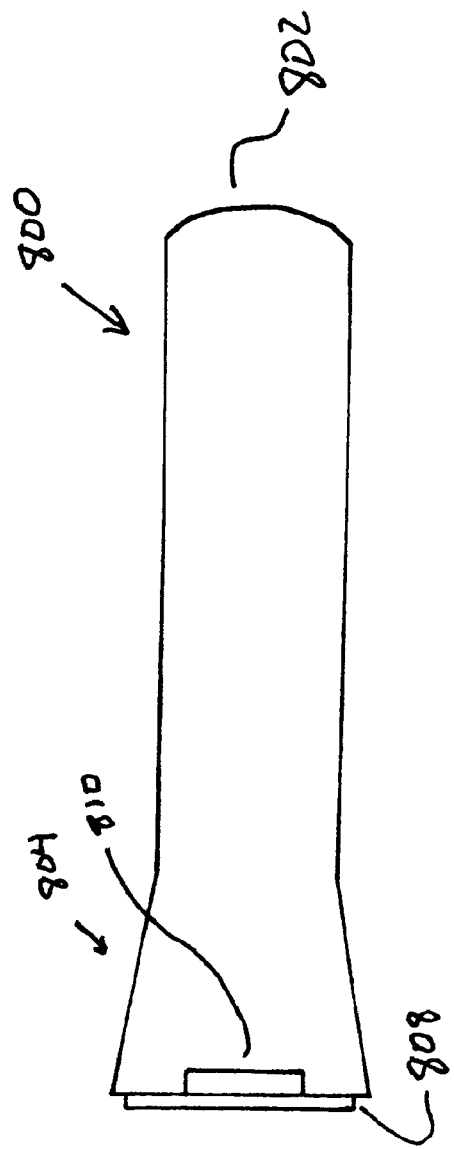

CAMERA AND LIGHT APPARATUS

BACKGROUND OF THE INVENTION

Lay persons have conducted at-home medical inspections for many years. Virtually every sick child has been subjected to a flashlight being thrust into its mouth as a parent attempts to ascertain the absence or presence of clinical signs of various ailments. These same flashlights are used to conduct inspections of the child's ears. Of course, at-home medical inspections are not limited to inspections of another individual. Individuals commonly grab the nearest flashlight and position themselves in odd positions in front of a mirror in order to perform self-inspections, such as to view a sore throat, for example. Unfortunately, the presence of the flashlight, while necessary to be able to see anything in the dark recess of a throat, presents a cumbersome obstacle to the vision of the individual performing the inspection.

The growing concern with various forms of skin cancer has presented additional difficulties, as it is necessary to look at virtually every inch of one's skin if a thorough inspection is to be conducted. Not only does this present difficulty in areas of the back, shoulders and head, but inspection in various private areas is virtually impossible.

Various hand held instruments for use by physicians or dentists during examination of a patient have been known for many years. It has also been known to use micro-cameras and micro-video cameras in the performance of surgical procedures. These devices, however, tend to be extremely complicated and expensive to manufacture. Moreover, it is often difficult for a layperson to use these devices in a manner that allows for the self inspection of the type needed in searching for signs of skin cancer and other diseases.

More recently, the decrease in expense and the continuing miniaturization of components has allowed for expanded uses of micro-cameras and micro-video cameras. For example, these devices may be used in surveillance systems and home security systems. It is even known to use micro-cameras and micro-video cameras mounted in glasses or mounted onto one's head so as to record what one is seeing. These devices are particularly popular for use by tourists and individuals involved in other recreational activities such as sky-diving and amusement rides. These devices are not acceptable for self inspections, in part, because a light source is still required for inspection of certain areas.

It is desirable, therefore, to provide a device which allows for illumination of an object while capturing an image of the object. It is desired that the device be easy for lay persons to use, especially when conducting inspections of themselves or others for diagnosis of medical conditions. It is further desired that the device be easily configured for a variety of such inspections. Moreover, it is desired that the device be of simple and inexpensive construction. It would be further advantageous if the device were capable of transmitting the images captured to a remote location.

BRIEF SUMMARY OF THE INVENTION

In accordance with the present invention, a combination light and camera is provided which overcomes the disadvantages of the prior art by providing an easy to use camera and light suitable for personal inspections. In one embodiment, a miniature video-camera is embedded in the lens of a hand-held flashlight. Video signals from the miniature video-camera may be viewed on a television set by using a standard RCA plug. Alternatively, a miniature transmitter may be used to transmit the video signals to a remote viewing location. The present invention also comprises a variety of lens forms which may be used in conjunction with the combination camera and light to aid in performing personal inspections. In certain configurations, the present invention is useful as a hand-held personal inspection device, capable of providing a video record of where a flashlight is aimed.

The invention provides a device which allows for illumination of an object while capturing an image of the object. A device according to the present invention is easy for lay persons to use and to configure for use, especially when conducting inspections of themselves or others for diagnosis of medical conditions. The present invention is also simple and inexpensive to manufacture and can easily be configured to transmit images captured to a remote location for viewing and/or recordation.

BRIEF DESCRIPTION OF THE DRAWINGS

FIG. 7 is a laid open side plan view of one embodiment of a lens in accordance with the present invention.

FIG. 8 is a laid open side plan view of an alternative embodiment of a lens in accordance with the present invention.

DETAILED DESCRIPTION OF THE INVENTION

Figure 1:
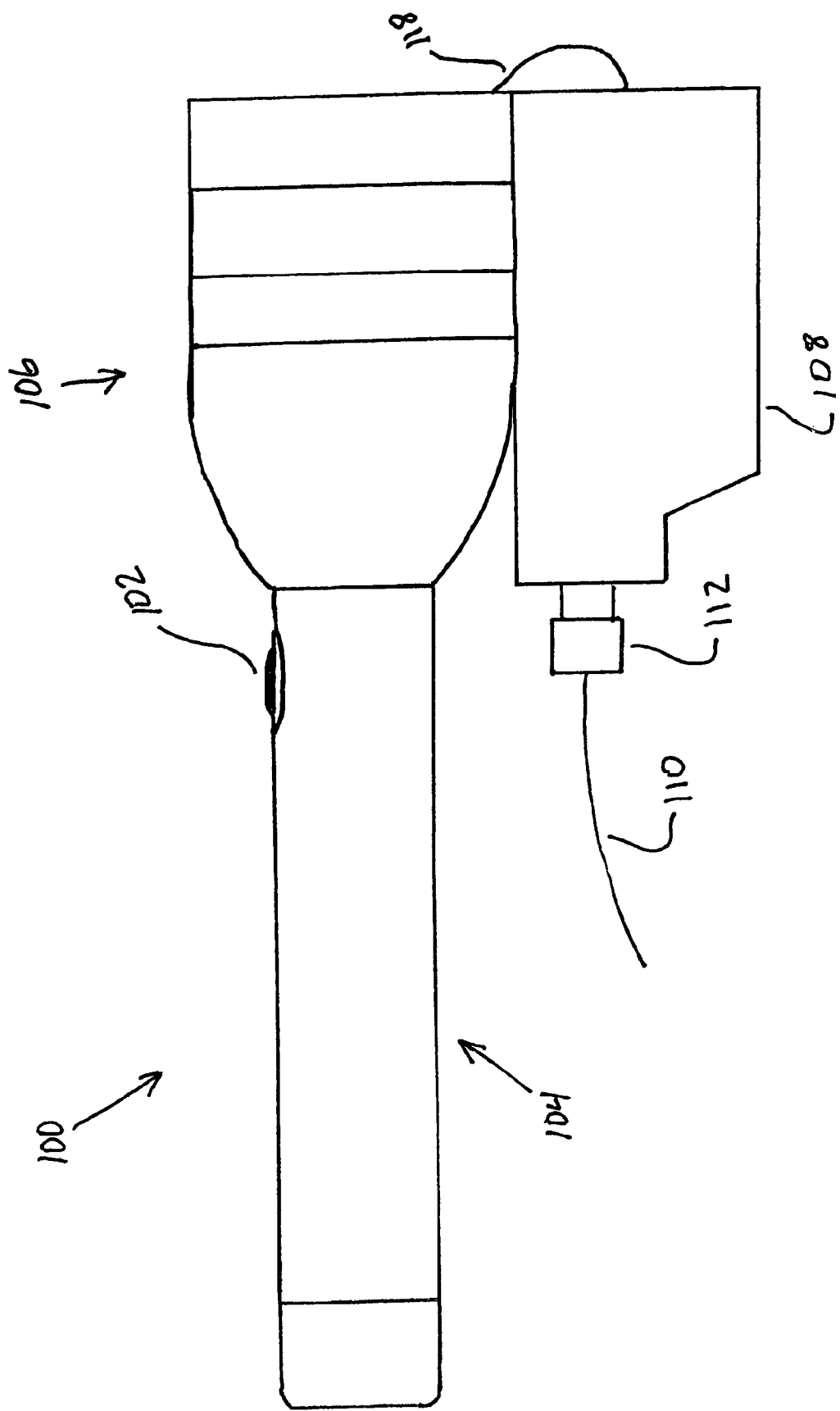
FIG. 1 is a side plan view in accordance with an exemplary embodiment of the present invention.

An exemplary embodiment of the present invention is described in reference to FIG. 1. Referring to FIG. 1, a side plan view of one embodiment of the invention is shown. Flashlight 100 comprises on-off button 102, battery section 104, and lens section 106 at the forward end of flashlight 100. In this embodiment, lens section 106 comprises a means for emitting a light beam in a generally forward path. Transmitter 108 is attached to lens section 106 and includes antenna 110 and on-off button 112 which controls miniature video-camera 116 shown in FIG. 2. Transmitter 108 is a wireless transmitter capable of transmitting images captured by video-camera 116 to a remote location. Wireless transmitter 108 may be of the type model S130356 and video-camera 116 may be of the type S130351, both commercially available from Intplus, S.L. of Sevila, Spain.

Those of skill in the relevant art will realize, however, that a number of alternative cameras and transmitters exist. According to one embodiment, the camera and transmitter comprise a single unit, such as is available in camera transmitter model AVX434S2, commercially available from Supercircuits, Inc. of Liberty Hill, Tex. Moreover, the camera may be a still camera or a video camera. These and other alternative embodiments being within the scope of the present invention. The salient feature of the camera is that it is of a reduced size, as will be discussed below.

Figure 2:
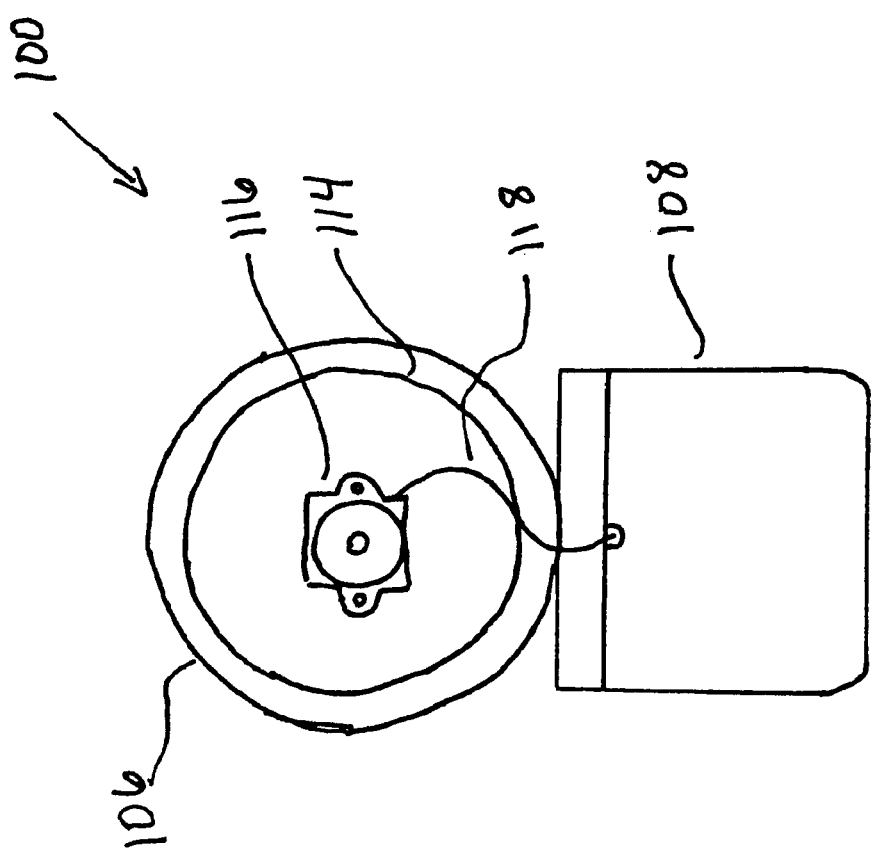
FIG. 2 is a front plan view of the embodiment of the invention shown in FIG. 1.

FIG. 2 is a front plan view of flashlight 100. Lens section 106 comprises lens 114. Miniature video-camera 116 is embedded in lens 114. The output of miniature video-camera 116 is provided to transmitter 108 by wire 118. Because it is of a reduced size, miniature video-camera 116 may be placed directly in the beam of light produced by flashlight 100 without unduly interfering with the beam of light emitted by flashlight 100. Accordingly, flashlight 100 may be positioned extremely close to an object to be imaged, without loss of illumination. Additional benefits resulting from the placement of miniature video-camera 116 within lens 114 will be discussed below.

Figure 3:
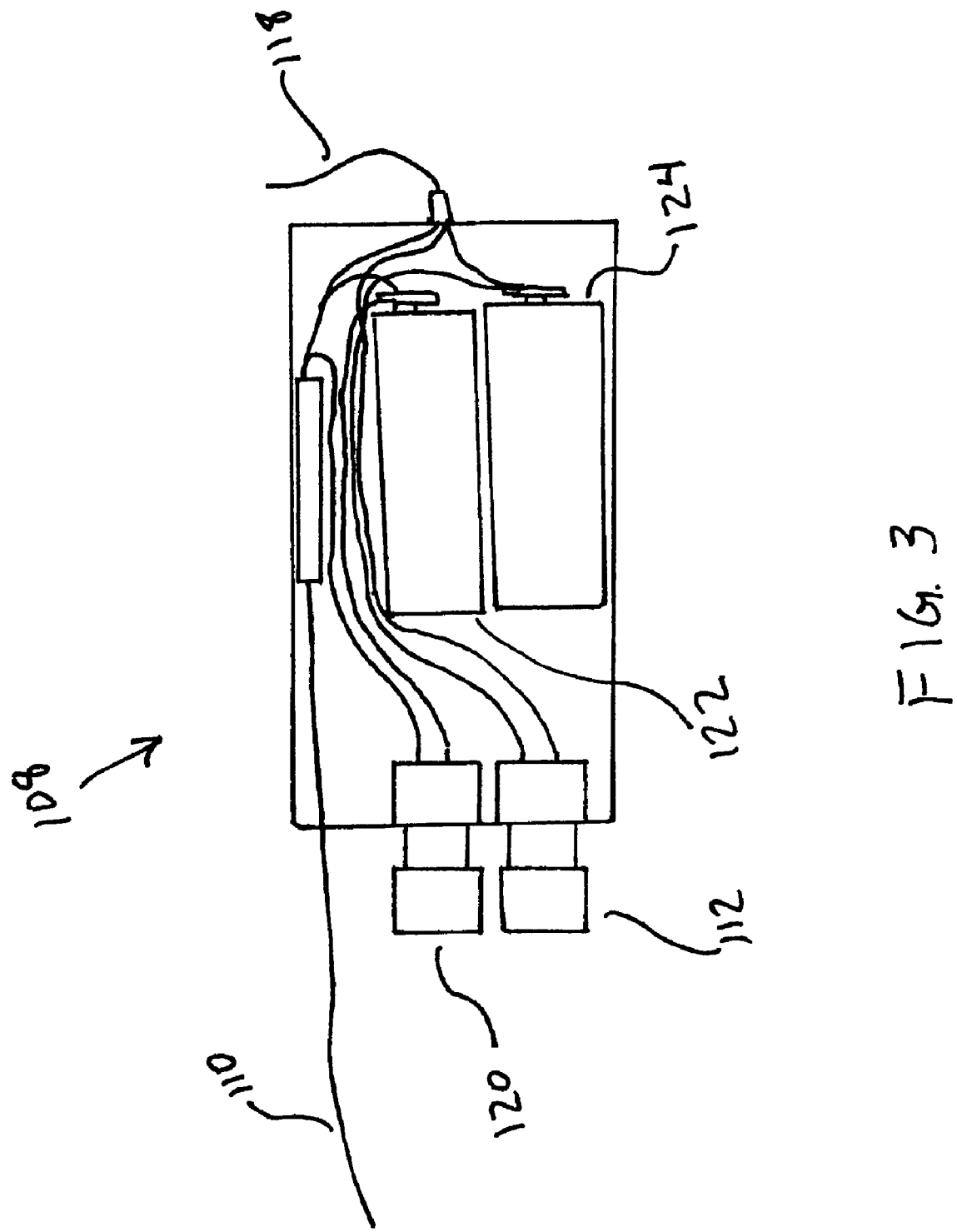
FIG. 3 is a laid open top plan view of the transmitter of the embodiment of the invention shown in FIG. 1 and FIG. 2.

FIG. 3 is a laid open top plan view of transmitter 108. Transmitter 108 comprises on-off button 120 which controls power to transmitter 108. Power for transmitter 108 is supplied by battery 122. Battery 124 supplies power to miniature video-camera 116.

Figure 4:
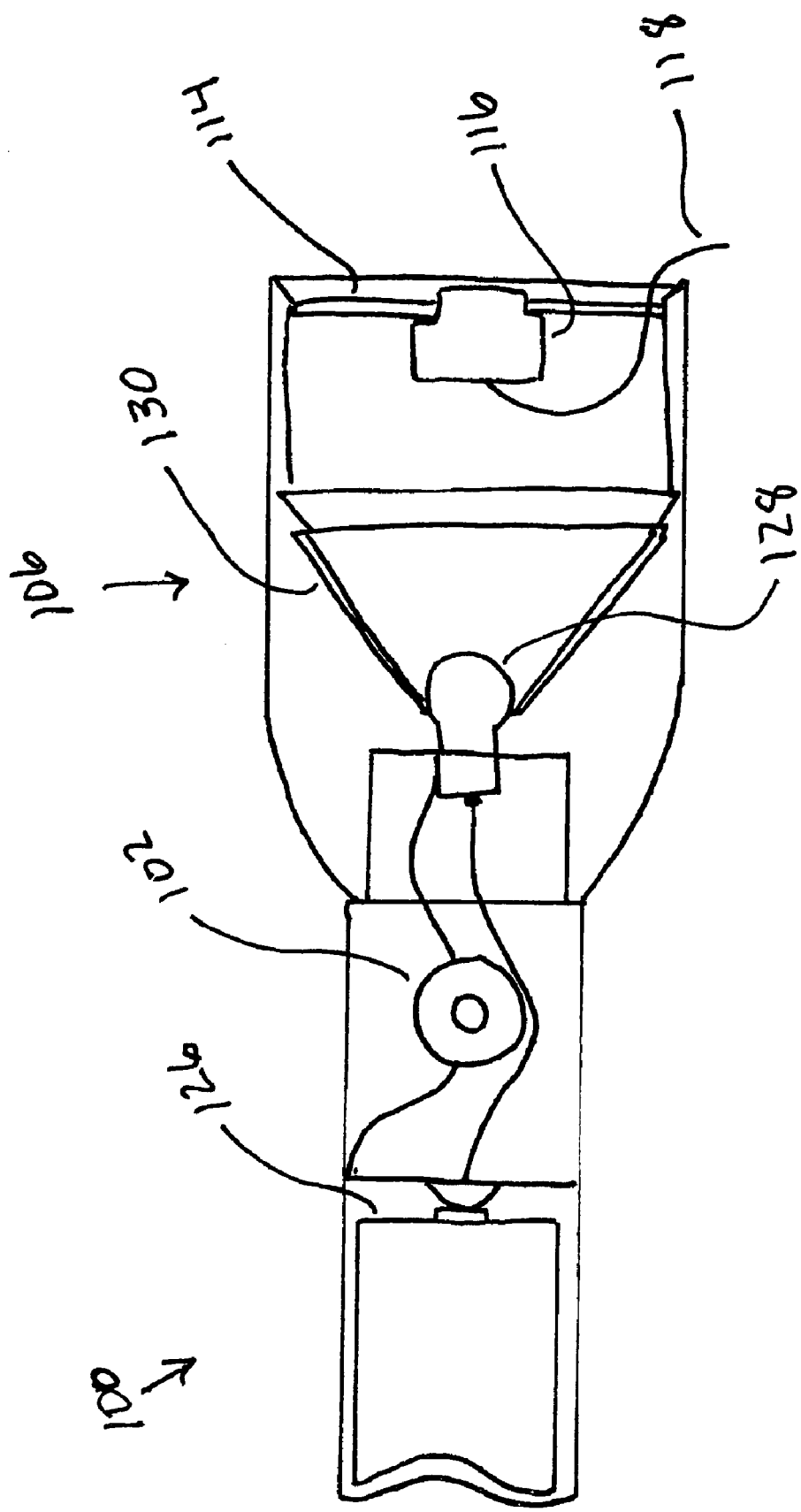
FIG. 4 is a partial laid open top plan view of the flashlight of the embodiment of the invention shown in FIG. 1 and FIG. 2.

Referring to FIG. 4, which is a partial laid open top plan view of flashlight 100, battery 126 supplies power to light emitting device 128 and is controlled by on-off button 102. Those of skill in the art will realize that for certain applications a battery operated device is not needed. Accordingly, power may alternatively be provided by hard wiring the device into another power source or through the provision of a plug for connecting to a power source. Moreover, the camera, transmitter and light emitting device may share a common power source. These and other variations being within the scope of the present invention.

Also shown in FIG. 4 is reflector 130. Reflector 130 in this embodiment works in conjunction with light emitting device 128 and lens 114 to project a beam of light in a generally forward direction. The present invention may be practiced with a wide variety of means for projecting light in a generally forward direction. For example, a reflector may not be desired for a particular application. Alternatively, a parabolic or other shaped reflector may be used. Moreover, light emitting device 128 may be a candescent bulb, an incandescent bulb or light emitting diode. These and other embodiments being within the scope of the present invention.

Figure 5:
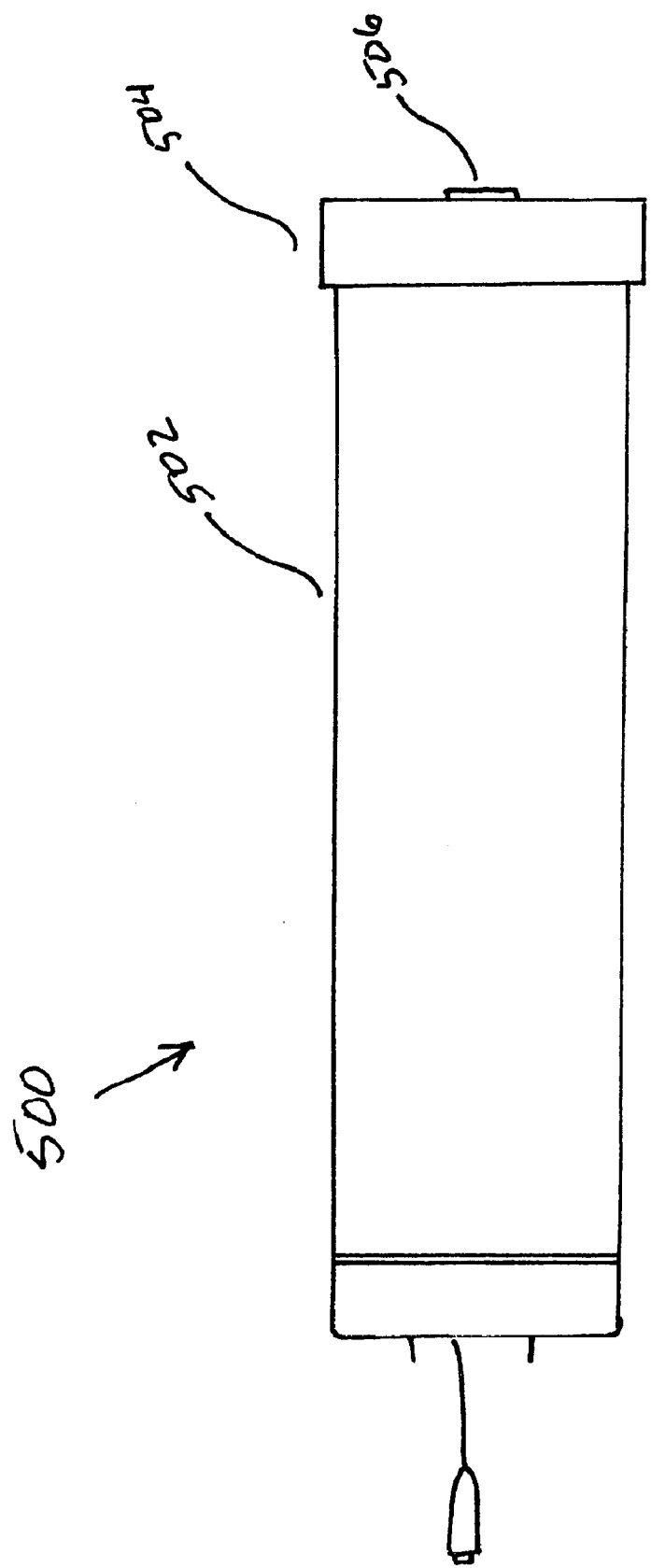
FIG. 5 is a side plan view of an alternative embodiment of the present invention without a transmitter.
Figure 6:
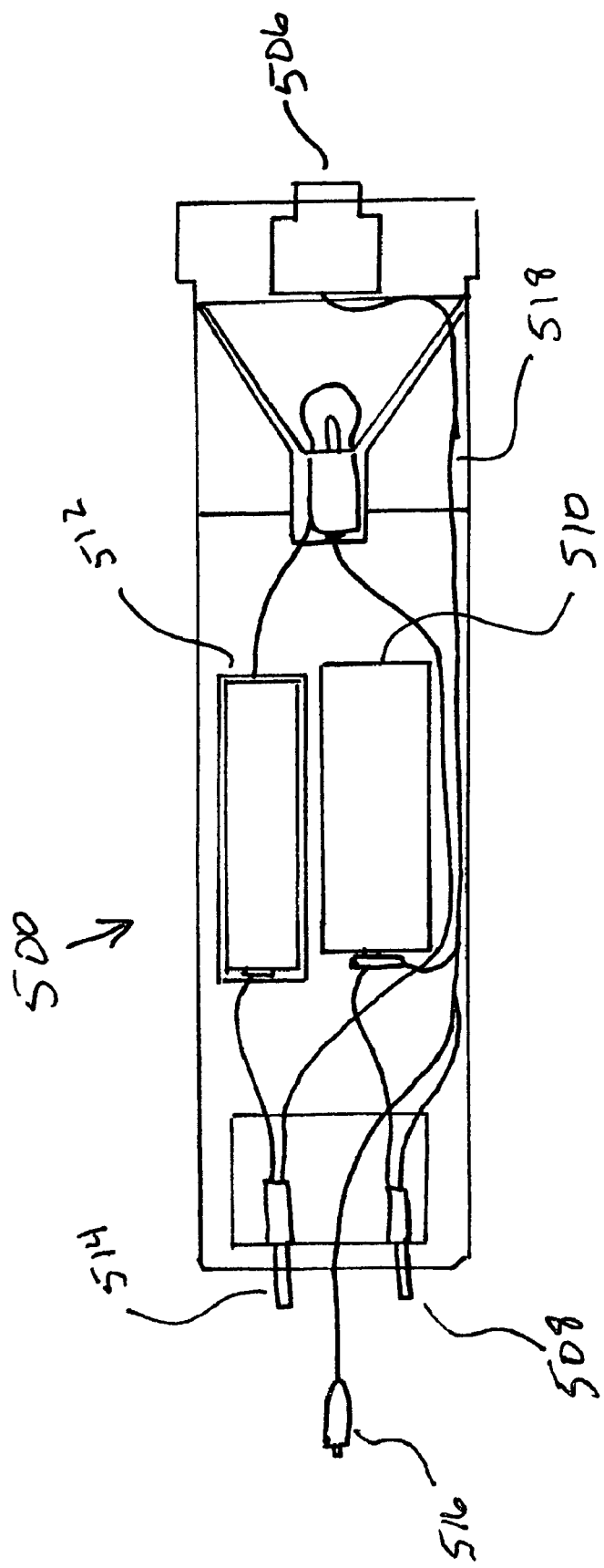
FIG. 6 is a partial laid open top plan view of the embodiment of the invention shown in FIG. 5.

An alternative embodiment of the invention is shown in FIG. 5. In this embodiment, flashlight 500 comprises battery section 502, lens section 504 and miniature video-camera 506. Referring now to FIG. 6, miniature video-camera 506 is powered by battery 510 as controlled by on-off button 508. Light source 510 is powered by battery 512 and controlled by on-off button 514. Video output from miniature video-camera 506 is available at RCA plug 516 through wire 518.

The present invention further comprises means for directing light to and from an object to be imaged. Alternative means are shown in FIGS. 7 and 8. Referring to FIG. 7, lens 700 is designed to provide illumination to an area to be inspected through tip 702. Tip 702 is much smaller than lens 114 of flashlight 100. Thus, tip 702 may easily fit within smaller orifices such as an individual's throat so as to inspect the throat of the individual. Alternatively, tip 702 may be used to look within an individual's ear. Of course, tip 702 and other smaller sized lenses can be used to look within cracks and crevices to look for lost items or for doing structural inspections.

Base 704 of lens 700 is designed to focus the light coming from lens 114 into tip 702. Accordingly, base 704 expands from tip 702 to a circumference about the size of lens 114. Inset 708 of base 704 is designed to fit within lens section 106 so as to provide optical communication between lens section 106 and lens 700. Thus, light beams emitted from flashlight 100 pass into and through lens 700. Moreover, when lens 700 is inserted into lens section 106, miniature video-camera 116 at the forward end of flashlight 100 extends into recess 710 allowing base 704 to fit flush against lens 114. Thus, optical communication is provided between lens 700 and miniature video-camera 116.

The location of miniature video-camera 116 within lens section 106 allows for a single lens to be used which both directs light to the area to be viewed, and allows for the emitted or reflected light to be returned to miniature video-camera 116. This is a significant advantage, as a variety of lens shapes can be easily fit within lens section 106 depending on the desired application. Moreover, the size of the lens is reduced, as it need only be sized to fit over lens section 106. Furthermore, because the camera is within the emitted light beam, the device may be placed very close to an object to be imaged without loss of illumination. Of course, at close range it may be desired to reduce the illumination level of the emitted light beam. In these situations, a dimmer switch may be utilized, such use being within the scope of the present invention.

In order to pass light, such that the performance of miniature video-camera 506 is not significantly degraded, lens 700 must be manufactured from a material that exhibits high clarity. Moreover, it is advantageous if lens 700 is manufactured from a material that can be easily disinfected and has high tensile strength. One such material is available in the form of cast acrylic block such as poly methyl methacrylate, commercially available from Industrial Plastic Supply, Inc. of Anaheim Calif. The block may be fashioned into the desired lens shape by milling and polishing. Lens 700 thus passes the emitted light beam, directing it toward the object to be imaged, and passes reflected or emitted light from the object to be imaged to miniature video-camera 116.

FIG. 8 shows an alternative lens. Base 804 of lens 800 is designed to focus the light coming from lens 114 into tip 802. Accordingly, base 804 expands from tip 802 to a circumference about the size of lens 114. Lens 800 is designed to provide illumination to an area to be inspected through tip 802. Tip 802 is somewhat smaller than lens 114 of flashlight 100, but significantly larger than tip 702 of lens 700. Thus, tip 802 is useful for inspecting areas such as the back and shoulders of an individual. Tip 802 may also be sized such that it is useful for vaginal and rectal inspections.

Continuing with the description of lens 800, inset 808 of base 804 is designed to fit within lens section 106. When lens 800 is inserted into lens section 106, miniature video-camera 116 extends into recess 810 allowing base 804 to fit flush against lens 114.

Those of skill in the art will realize that as described herein, the present invention provides significant advantages over the prior art. The invention provides a device which allows for illumination of an object while capturing an image of the object, even at very close range. The present invention is easy for lay persons to use and to configure for use, especially when conducting inspections of themselves or others for diagnosis of medical conditions. The present invention is also simple and inexpensive to manufacture and can easily be configured to transmit images captured to a remote location for viewing and/or recordation. Other objects and features of the present invention will be apparent to those of skill in the art in consideration of the above description, the accompanying drawings, and the following claims.

While the present invention has been described in detail with reference to certain exemplary embodiments thereof, such is offered by way of non-limiting example of the invention, as other versions are possible. It is anticipated that a variety of other modifications and changes will be apparent to those having ordinary skill in the art and that such modifications and changes are intended to be encompassed within the spirit and scope of the invention as defined by the following claims.

I claim:

1. A device for simultaneously illuminating and imaging an object, comprising:
   a light emitting means operable to emit a light beam generally from the light emitting means toward the object, and wherein the object is located in front of the light emitting means; and
   a camera comprising a lens and a camera housing module, the lens and the camera housing module located entirely within the light beam.

2. The device of claim 1 wherein the light emitting means comprises a light emitting device; and
   a reflector arranged about the light emitting device such that the path of an emitted light beam is in the generally forward direction.

3. A device for simultaneously illuminating and imaging an object, comprising:
   a means for emitting a light beam in a generally forward path;
   a camera located within the forward path of an emitted light beam form the means for emitting a light beam; and
   a means for directing light to and from an object to be imaged, the means for directing light in optical communication with the means for emitting a light beam and the camera.

4. The device of claim 3, wherein the means for directing light is sized so as to be at least partially inserted into an orifice.

5. The device of claim 4, wherein the device is sized to be at least partially inserted into an orifice selected from among the following group:
   an ear canal
   a mouth;
   an anal canal; and
   a vulva.

6. The device of claim 3, wherein the means for directing light is shaped so as to facilitate viewing of an individual's back when the individual is manipulating the device.

7. The device of claim 3, wherein the means for directing light comprises poly methyl methacrylate.

8. A device for simultaneously illuminating and imaging an object, comprising:
   a means for emitting a light beam in a generally forward path;
   a camera located within the forward path of an emitted light beam from the means for emitting a light beam; and
   a wireless transmitter in communication with the camera such that images captured by the camera can be transmitted to a remote location.

9. The device of claim 8, wherein the camera comprises a video camera.

10. The device of claim 8, further comprising a means for directing light to and from an object, the means for directing light in optical communication with the means for emitting a light beam and the camera.

11. The device of claim 10, further comprising a dimmer switch, the dimmer switch in electrical communication with the means for emitting a light beam.

* * * * *